(12) United States Patent
Höglund et al.

(10) Patent No.: US 8,137,391 B2
(45) Date of Patent: Mar. 20, 2012

(54) HIGH VISCOSITY COMPOSITION

(75) Inventors: Christer Höglund, Karlstad (SE); Dag Kryzaniak, Karlstad (SE)

(73) Assignee: Becare Orthopedic Thermal Care AB, Karlstad (SE)

( * ) Notice: Subject to any disclaimer, the term of this patent is extended or adjusted under 35 U.S.C. 154(b) by 589 days.

(21) Appl. No.: 12/304,054

(22) PCT Filed: May 25, 2007

(86) PCT No.: PCT/SE2007/000504
§ 371 (c)(1),
(2), (4) Date: Jan. 28, 2009

(87) PCT Pub. No.: WO2007/142571
PCT Pub. Date: Dec. 13, 2007

(65) Prior Publication Data
US 2010/0030305 A1      Feb. 4, 2010

(30) Foreign Application Priority Data
Jun. 9, 2006    (SE) .................................... 0601273

(51) Int. Cl.
*A61F 7/00*    (2006.01)
(52) U.S. Cl. ......................................................... 607/96
(58) Field of Classification Search .................. 424/443; 602/41, 67; 604/304; 607/96
See application file for complete search history.

(56) References Cited

U.S. PATENT DOCUMENTS

| | | | |
|---|---|---|---|
| 3,865,544 A * | 2/1975 | Keil ................................. 8/581 |
| 4,010,110 A * | 3/1977 | Cosentino et al. ............ 252/180 |
| 4,404,820 A * | 9/1983 | Romaine ........................ 62/530 |
| 4,530,220 A * | 7/1985 | Nambu et al. .................. 62/530 |
| 5,935,595 A * | 8/1999 | Steen ............................ 424/443 |
| 6,217,606 B1 * | 4/2001 | Portnoy et al. ................. 607/96 |
| 6,774,181 B1 * | 8/2004 | Bechara et al. ................ 525/66 |

FOREIGN PATENT DOCUMENTS

GB            2 347 866         9/2000

OTHER PUBLICATIONS

WO2004/085729, Sanyo Chem IND LTD, Oct. 7, 2004.*
WO2004/069955, Daikin IND LTD, Aug. 19, 2004.*
WO2004/069935, Daikin IND LTD, Dikin IND LTD, Aug. 19, 2004.*
EP10600481, Daikin IND LTD, Nov. 30, 2005.*
EP1245634, Daikin IND LTD, Oct. 2, 2002.*
WO2000/47186, Supra Tech Pharma Inc., Aug. 17, 2000.*
WO2000/04071, Arco Chem Tech, Jan. 27, 2000.*
GB2347866, Alternative Thermal Therapies, Sep. 20, 2000.*
Written Opinion of the International Search Authority dated Sep. 19, 2007 in PCT Application No. PCT/SE2007/000504, 4 pgs.

* cited by examiner

*Primary Examiner* — Manuel Mendez
(74) *Attorney, Agent, or Firm* — Nixon & Vanderhye P.C.

(57) ABSTRACT

A high viscosity composition which according to the invention comprises at least one polyoxyethylene-polyoxypropylene-block copolymer (poloxamer) having the structural formula $HO(C_2H_4O)_a (C_3H_6O)_b (C_2H_4O)_a H$ and having an average molecular weight of above 6000; at least one additional polymer having an average molecular weight of above 150000, and a dispersion medium, comprising at least one freezing point depressing dispersant and at least one freezing point non-depressing dispersant. The composition is heatable above the body temperature of a mammal and coolable below 0° C. within a predetermined temperature range.

9 Claims, No Drawings

HIGH VISCOSITY COMPOSITION

This application is the U.S. national phase of International Application No. PCT/SE2007/000504 filed May 25, 2007 which designated the U.S. and claims priority to Swedish Patent Application No. 0601273-6 filed Jun. 9, 2006, the entire contents of each of which are hereby incorporated by reference.

The present invention relates to a high viscosity composition.

The invention also relates to an article for application onto an extremity of a mammal, optionally for absorption or emission of heat from and to the extremity, respectively, comprising a fluid-impervious cover of a flexible material and a high viscosity composition being enclosed in the cover.

The object of the present invention is to provide a high viscosity composition which preserves a highly viscous state within a wide temperature range extending on both sides of the normal body temperature of a mammal.

The high viscosity composition according to the invention is characterized in that it comprises:
- at least one polyoxyethylene-polyoxypropylene-block copolymer (poloxamer) having the structural formula

$HO(C_2H_4O)_a (C_3H_6O)_b (C_2H_4O)_a H$ and having an average molecular weight of above 6000;
- at least one additional polymer having an average molecular weight of above 150000; and
- a dispersion medium comprising at least one freezing point depressing dispersant and at least one freezing point non-depressing dispersant, said composition being heatable above body temperature and coolable below 0° C. within a predetermined temperature interval.

Polyoxyethylene-polyoxypropylene-block copolymers, generally designated poloxamers, have the general formula

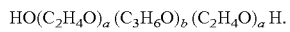

$HO(C_2H_4O)_a (C_3H_6O)_b (C_2H_4O)_a H$.

Poloxamers are manufactured in a variety of different grades which are commercially available and different with respect to molecular weight and the ratio between the number of oxyethylene units a and the number of oxypropylene units b. In the preferred embodiments of the poloxamer, the value $\bar{a}$ is substantially larger than the value b in said structural formula and the average molecular weight is above 10000. A poloxamer, which is preferred in the composition according to the invention, is available under the designation poloxamer 407, which has a molecular weight of 9840-14600 and where the number of units a is 101 and the number of units b is 56. According to a particularly preferred embodiment, poloxamer 407 is included in an amount of 13-15% by weight of the composition.

In contrast to normal polymers, a high-molecular poloxamer is readily fluid at low temperatures, but will get a highly increased viscosity at higher temperatures. Poloxamer 407 which is dispersed in water in an amount of 25%, for instance, is fluid up to about 20° C. and will then transform into a stable gel, which is permanent up to about 70° C., whereas a 16% solution of this poloxamer is fluid up to about 30° C. and will then form a gel, which is permanent up to about 60° C. At lower levels of this polymer, however, no gel is formed. Poloxamer is preferably included in an amount of at least 10% by weight of the composition and said at least one additional polymer in an amount of at least 5% by weight of the composition. Most preferably, the poloxamer is included in an amount of 10-25% by weight of the composition and said at least one additional polymer in an amount of 5-20% by weight of the composition.

Since it is desired that a high viscosity composition also should be useful at those lower temperatures where the poloxamer normally is readily fluid, i.e. a viscosity which is below the viscosity of e.g. syrup, it is a task of the invention also to find an additional component, which provides an excellent viscosity also at said lower temperatures. An additional polymer having an average molecular weight of above 150000 has proved to be such an additional component.

Examples of such high-molecular polymers are cellulose derivatives, such as carboxymethyl cellulose, ethyl cellulose, hydroxyethyl cellulose and hydroxypropylmethyl cellulose and sodium and calcium salts thereof; alginic acid/alginates, such as sodium alginate and propylene glycol alginate; carboxy polymethylenes, which are designated carbomers and are high-molecular polymers of acrylic acid crosslinked with various chemical compounds, such as alkyl ethers of sucrose or pentaerythritol, e.g. the commercial products under the designation "Carbopol"; polyvinyl alcohol; and polyvinylpyrrolidone. Among these high-molecular polymers, polyvinylpyrrolidone, having an average molecular weight of about 1 million, is preferred. When carboxy polymethylene is used, it preferably has an average molecular weight of above 1 million.

Since it is required that the high viscosity composition should be able to cool down to a low temperature below 0° C., the dispersion medium has to comprise at least one freezing point depressing dispersant. It has surprisingly been found that the use of such a freezing point depressing dispersant for said two types of polymers results in an increased viscosity of the composition within the low temperature range from 0° C. and upwards, said increased viscosity furthermore being preserved into the low temperature range below 0° C. There is also a viscosity increase within the upper temperature range, which can result in gelation or improved gel strength and a lowering of the gelling point, all as calculated in relation to a corresponding polymer mixture with only water as a dispersant. Examples of suitable freezing point depressing dispersants are propylene glycol, ethylene glycol, butylene glycol and glycerol. The amounts of the two polymers can be reduced by the use of a freezing point depressing dispersant, since it influences favourably the formation of a gel. Furthermore, it has a valuable antimicrobial effect.

An additional component of the high viscosity composition according to the invention is a freezing point non-depressing dispersant, and which preferably is water or a higher alcohol having a boiling point above 100° C., or a mixture of these, wherein water is most preferred.

According to a preferred embodiment, the freezing point depressing dispersant constitutes 20-90% of the dispersion medium and the freezing point non-depressing dispersant 80-10% thereof.

According to a preferred embodiment, the high viscosity composition according to the invention comprises a strong electrolyte, which is selected from the group consisting of sodium, potassium, calcium and magnesium salts, preferably a chloride salt. The electrolyte is included in an amount of 2-7% by weight of the composition. The electrolyte is usually added as a saturated solution. The electrolyte lowers the gelling point of the composition even further, which implies that the amounts of the two polymers can be reduced to a corresponding degree, depending on the form of the composition which is desired within the wide temperature range in question where the composition is intended to be used. According to one embodiment, the solvent of the electrolyte is constituted of the water being present or added as a dispersant. According to another embodiment, the electrolyte is added as a saturated water solution, wherein this water also constitutes the entire or part of the amount of water constituting said freezing point non-depressing dispersant, said water also constituting part of or the entire amount of said freezing point non-depressing dispersant, which is included in an amount constituting at least 10% of the dispersion medium.

According to a particularly preferred embodiment of the high viscosity composition, it comprises 10-25% by weight of poloxamer 407, 5-20% by weight of polyvinylpyrrolidone, 50-70% by weight of propylene glycol and 2-7% by weight of sodium, potassium, calcium or magnesium salt, calculated on the weight of the composition, and such an amount of water which is required in order to obtain a saturated solution of said salt, said water also constituting part of or the entire amount of said freezing point non-depressing dispersant, which is included in an amount constituting at least 10% of the dispersion medium.

The invention also relates to an article, that may be in form of a cushion or similar, for application onto an extremity of a mammal, optionally for absorption or emission of heat from and to the extremity, respectively, said article comprising a fluid-impervious cover of a flexible material being conformable by internal and external pressure action, and also a high viscosity composition according to the invention enclosed in the cover.

The invention will be described further by means of the examples below.

EXAMPLE 1

A high viscosity composition being suited for treatment of parts of the body is prepared of the following constituents and in the amounts indicated:

| Constituents | Weight, grams |
|---|---|
| Propylene glycol | 2995 |
| Polyvinylpyrrolidone | 550 |
| Poloxamer | 740 |
| Saturated NaCl-solution | 715* |
| | 5000 |

*185 grams of NaCl in 530 grams of water.

As a polyvinylpyrrolidone, the one being sold under the trade name Kollidon 90F, having an average molecular weight of 1000000, is selected. As a poloxamer, the one being sold under the trade name Lutrol 127 (poloxamer 407), having an average molecular weight of 12600, is selected. The electrolyte water (530 g) is also counted as a dispersant. The constituents are mixed in the above-mentioned order by means of suitable equipment. A highly viscous mixture, exhibiting a gel structure and a density of 1.1, is obtained. The gel composition is filled into baglike covers of a suitable shape and a suitable fluid-impervious, flexible material, and then the bags are fluid-imperviously sealed in order to provide articles in form of cushions containing the gel composition. A first group of the cushions is heated to different, high temperatures, whereas a second group is cooled to different, low temperatures. It turns out that the gel composition preserves its gel structure up to 70° C. and down to −20° C. and within the entire temperature interval of from 70° C. to −20° C. Owing to the preserved gel structure, the cushions with enclosed cooled or heated composition will conform intimately to the outline of the parts of the body where they are applied, and the internal surface layer of each cushion instantaneously changes its outline to the outline of the part of the body. Even if the gel is soft and readily mouldable, it provides a certain firmness, which is advantageous when treating a recess or cavity in the body outline in that the gel not only fills up the entire recess or cavity but also provides a certain advantageous pressure via the cover wall against the skin in the recess or cavity, so that an intimate contact between the cushion and the skin is obtained also in such areas, said intimate contact facilitating the transfer of heat from or to the part of the body also in said area. Furthermore, a study was conducted in order to establish the capability of the gel composition to retain its heat content and the capability to delay the absorption of heat from the environment having room temperature, respectively. Two beakers were each filled with 80 grams of the gel composition prepared in Example 1. One beaker was placed in a freezer and the other in a heating cabinet. When the study started, the gel removed from the freezer had a temperature of −19° C., whereas the gel removed from the heating cabinet had a temperature of 60° C. The subsequent temperature changes over time are evident from the table below.

TABLE

| Gel from freezer | | Gel from heating cabinet | |
|---|---|---|---|
| $t_0$ | −19° C. | $t_0$ | +60° C. |
| 12 min | −8° C. | 10 min | +54° C. |
| 25 min | 0° C. | 22 min | +46° C. |
| 40 min | +9° C. | 42 min | +40° C. |
| | | 77 min | +30° C. |
| | | 102 min | +28° C. |

The results show that the gel has an excellent capability of retaining its heat content and an excellent capability of delaying the absorption of heat from the environment, respectively. Accordingly, the gel is very well suited for being used on the extremities of a mammal for heat emission to the extremity or heat absorption from the extremity as required.

In the two examples below, part of the propylene glycol is replaced by water in different proportions.

EXAMPLE 2

| Constituents | Weight, grams |
|---|---|
| Propylene glycol | 80 |
| Water | 40 |
| Polyvinylpyrrolidone | 22 |
| Poloxamer | 30 |
| Saturated NaCl-solution | 31* |
| | 203 |

*8 grams of NaCl in 23 grams of water.

The polyvinylpyrrolidone and the poloxamer are the same as in Example 1. The constituents are mixed in the above-mentioned order by means of suitable equipment. A highly viscous mixture, being very thick and viscous, is obtained, and proves to preserve its thick consistency when being heated and cooled to different temperatures within the entire temperature range in question. It is useful for treating parts of the body in the same way as described for the composition according to Example 1.

EXAMPLE 3

| Constituents | Weight, grams |
| --- | --- |
| Propylene glycol | 40 |
| Water | 80 |
| Polyvinylpyrrolidone | 22 |
| Poloxamer | 30 |
| Saturated NaCl-solution | 31* |
|  | 203 |

*8 grams of NaCl in 23 grams of water.

The polyvinylpyrrolidone and the poloxamer are the same as in Example 1. The constituents are mixed in the above-mentioned order by means of suitable equipment. A highly viscous mixture, also in this case being very thick and viscous, is obtained, and proves to preserve is thick consistency when being heated and cooled to different temperatures within the entire temperature range in question. It is useful to be applied, in enclosed form, onto the extremity of a mammal in the same way as described for the composition according to Example 1.

In a suitable enclosed shape, such as a cushionlike article, the composition is primarily suited for use on the extremities of a mammal in intimate contact with the outside of the extremity, optionally for heat absorption or heat emission from the extremity and to the extremity, respectively, such as treatment of the locomotion apparatus, joints, tendons, muscles and skeletal parts, in connection with different ailments, for influencing the blood circulation, for alleviating pain, for accelerating the healing process after fractures, for alleviating muscle aches after exercise, for achieving a feeling of relaxation, etc. An orthopedic article of the above-mentioned kind is anatomically designed. The expression "mammal" includes both humans and animals of a variety of species.

The invention claimed is:

1. A high viscosity composition for application onto extremities of a mammal, which is heatable above a body temperature of the mammal and coolable below 0° C. within a predetermined termperature interval and which comprises:
   a polyoxyethylene-polyoxypropylene-block copolymer having the structural formula

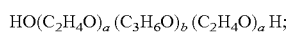

an additional polymer; and
   a dispersion medium, comprising at least one freezing point depressing dispersant and at least one freezing point non-depressing dispersant;
   wherein said polyoxyethylene-polvoxypropylene-block copolymer is poloxamer 407 having an average molecular weight of about 12600 and wherein a is 101 and b is 56,
   said poloxamer 407 being included in an amount of 10-25% by weight of the composition,
   said additional polymer is polyvinylpyrrolidone having an average molecular weight of about 1 million and being included in an amount of 5-20% by weight of the composition,
   said freezing point depressing dispersant is selected from the group consisting of propylene glycol, ethylene glycol, butylene glycol and glycerol,
   said freezing point non-depressing dispersant is selected from the group consisting of water and a higher alcohol having a boiling point above 100° C. and mixtures thereof, and
   said freezing point depressing dispersant constitutes 20-90% of the dispersion medium and the freezing point non-depressing dispersant constitutes 80-10% of the dispersion medium, and
   wherein the composition also comprises a strong electrolyte selected from the group consisting of sodium, potassium, calcium and magnesium chloride, said electrolyte being included in an amount of 2-7% by weight of the composition.

2. The high viscosity composition according to claim 1, wherein the poloxamer 407 is included in an amount of 13-15% by weight of the composition.

3. The high viscosity composition according to claim 1, wherein the freezing point non-depressing dispersant is water.

4. The high viscosity composition according to claim 1, wherein the freezing point non-depressing dispersant is water, and the solvent of the electrolyte is constituted of the water being present or added as dispersant.

5. The high viscosity composition according to claim 1, wherein the electrolyte is added as a saturated water solution, wherein this water also constitutes the entire or part of the amount of water constituting said freezing point non-depressing dispersant, said water also constituting a part of or the entire amount of said freezing point non-depressing dispersant, which is included in an amount constituting at least 10% of the dispersion medium.

6. An article for application onto extremities of a mammal, optionally for absorption or emission of heat from and to the extremity, respectively, comprising a fluid-impervious cover of a flexible material and a high viscosity composition being enclosed in the cover, characterized in that the high viscosity composition is the one according to claim 1.

7. The article according to claim 6, characterized in that it is in the form of a cushion.

8. Use of a composition according to claim 1 for application, in an enclosed form, onto the extremities of a mammal, optionally for heat absorption to the extremity or heat emission from the extremity.

9. The high viscosity composition according to claim 1, wherein said composition includes an amount of water which is required in order to obtain a saturated solution of said chloride salt, said water also constituting part or all of the said freezing point non-depressing dispersant, which is included in an amount constituting at least 10% of the dispersion medium.

* * * * *